US007198775B2

(12) United States Patent
El-Tamer et al.

(10) Patent No.: US 7,198,775 B2
(45) Date of Patent: *Apr. 3, 2007

(54) DETECTABLY LABELED PORPHYRIN COMPOUND FOR IDENTIFYING THE SENTINEL LYMPH NODE

(75) Inventors: Mahmoud El-Tamer, New York, NY (US); Rashid Fawaz, New York, NY (US); Theodore Wang, Tenafly, NJ (US); Ted Chaglassian, Forrest Hills, NY (US); Rola Saouaf, New York, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 161 days.

This patent is subject to a terminal disclaimer.

(21) Appl. No.: 10/199,660

(22) Filed: Jul. 19, 2002

(65) Prior Publication Data

US 2002/0192158 A1   Dec. 19, 2002

Related U.S. Application Data

(62) Division of application No. 09/583,359, filed on May 30, 2000, now Pat. No. 6,458,336.

(51) Int. Cl.
*A61B 5/055* (2006.01)

(52) U.S. Cl. .................. 424/9.362; 424/9.1; 424/9.3; 424/9.361

(58) Field of Classification Search ............... 424/1.65, 424/9.1, 9.6, 9.61, 1.69, 9.362, 9.3, 9.36; 540/145, 201, 122, 123, 131, 139
See application file for complete search history.

(56) References Cited

U.S. PATENT DOCUMENTS

| 4,996,312 | A | 2/1991 | Sakata et al. |
| 5,043,101 | A | 8/1991 | Gordon |
| 5,346,670 | A | 9/1994 | Renzoni et al. |
| 5,732,704 | A | 3/1998 | Thurston et al. |
| 6,022,526 | A | 2/2000 | Woodburn et al. |
| 6,217,844 | B1 | 4/2001 | Garnick |
| 6,458,336 | B1 * | 10/2002 | El-Tamer et al. .......... 424/1.65 |

FOREIGN PATENT DOCUMENTS

GB    2051817    1/1981

OTHER PUBLICATIONS

J.H. Weber, D.H. Busch, "Complexes Derived from Strong Field Ligands. XIX. Magnetic Properties of Transition Metal Derivatives of 4, 4', 4", 40'"—Tetrasulfophthalocyanine" *Inorganic Chemistry*, vol. 4(4), 469-471 (1965).
J.R. Rousseua, D. Autenrieth and J.E. Van Lier, "Synthesis, Tissue Distribution and Tumor Uptake of Tc-99m Tetrasulfophthalocyanine" *Int J Appl Radiat Isot*, 34:571-579 (1983).
D.W. Wong, "A Simple Chemical Method of Labeling Hematoporphyrin Derivative with Technetium-99m" *J Label Compd & Radiopheam* XX:351-361 (1983).
D.N. Krag, D.L. Weaver, J.C. Alex, J.T. Fairbank, "Surgical Resection and Radiolocalization of the Sentinel Lymph node in Breast Cancer Using a Gamma Probe" *Surgical Oncology*, 2:335-340 (1993).
A.E. Giuliano, D.M. Kirgan, J.M. Guenther, D.L. Morton, "Lymphatic Mapping and Sentinel Lymphadenectomy for Breast Cancer" *Annals of Surgery*, vol. 220. No. 3. 391-401 (1994).

* cited by examiner

*Primary Examiner*—Dameron L. Jones
(74) *Attorney, Agent, or Firm*—John P. White; Cooper & Dunham LLP

(57) ABSTRACT

A detectably labeled porphyrin compound for identifying a sentinel lymph node in patients, particularly those with cancer. A method of identifying a sentinel lymph node, comprising the steps of: injecting the detectably labeled porphyrin compound into a tumor, wherein the porphyrin compound is detectably labeled with a radiolabel which is a γ-emitting radioactive metal; and detecting radioactive emission or a color so as to detect and thereby identify the sentinel lymph node. A method of identifying a sentinel lymph node, comprising the steps of injecting the detectably labeled porphyrin compound into tissue surrounding a tumor, wherein the porphyrin compound is detectably labeled with a non-radioactive metal; and taking a series of magnetic resonance images to identify the sentinel lymph node by viewing the images showing the injected detectably labeled porphyrin compound.

8 Claims, No Drawings

DETECTABLY LABELED PORPHYRIN COMPOUND FOR IDENTIFYING THE SENTINEL LYMPH NODE

This application is a divisional of U.S. Ser. No. 09/583,359, filed May 30, 2000 now U.S. Pat. No. 6,458,336.

Throughout this application, various publications are referenced to by arabic numerals within parentheses. Disclosures of these publications in their entireties are hereby incorporated by reference into this application to more fully describe the state of the art to which this invention pertains. Full bibliographic citations for these references may be found at the end of this application, preceding the claims.

FIELD OF THE INVENTION

The present invention relates to a substance and method for identifying the sentinel lymph node in patients, particularly those with cancer. More particularly, the present invention relates to a detectably labeled porphyrin compound for identifying the sentinel lymph node.

BACKGROUND OF THE INVENTION

One of the major techniques for determining the prognosis of cancer, particularly breast cancer, involves examining the lymph nodes of the axilla or armpit of the patient. It is well known that a major aspect in assessing the stage of the cancer revolves around whether the cancer has spread to the lymph nodes. It is therefore important to have an effective technique for identifying the spread of the cancer through the lymphatic system.

In the lymphatic system of the human body, lymphatic fluid flows from the breast through the lymph channels and is filtered through the lymph nodes. The first stop is the "first lymph node" or the "sentinel lymph node." If the cancer has spread to the lymph nodes, the sentinel lymph node should be positive (i.e., cancerous). If the first lymph node is negative, it can be assumed that the rest of the lymph nodes are negative. Therefore, it is crucial that this first lymph node or sentinel lymph node be accurately identified.

A known technique for identifying the sentinel lymph node(s) involves the use of two substances: a blue substance and a radioactive substance. However, the sentinel lymph node may not be blue, or may not be radioactive, using this technique. This causes problems relating to the accuracy of the identification. Therefore, there is a need for an improved and more accurate technique for the identification of the sentinel lymph node.

In more detail, the known technique involves the two substances lymphazurin blue and sulfur colloid. There is a disadvantage to lymphazurin blue in that it cannot be radio-labeled. Another problem is that not only does the procedure require two substances, it also requires two separate injections. Therefore, there is a need for an improved and simplified technique for the identification of the sentinel lymph node.

Giuliano et al. describe the feasibility and accuracy of lymphatic mapping with sentinel lymphadenectomy in patients with breast cancer. (1) The conclusion was that lymphatic mapping can accurately identify the sentinel node in most patients.

Krag et al. describe the surgical resection and radiolocalization of the sentinel lymph node in breast cancer using a gamma probe. (2) It was concluded that radiolocalization and selective resection of sentinel lymph nodes is possible, and that the sentinel lymph node appears to predict correctly the status of the remaining axilla.

Wong describes a chemical method for labeling a hematoporphyrin derivative (HPD) with Technetium-99m. (3)

Rousseau et al. describe the synthesis, tissue distribution, and tumor uptake of $^{99}$Tc-labeled-tetrasulfophtalocyanine [$^{99}$Tc] TSPC, which was prepared by condensing sulfophthalic acid and pertechnetate in the presence of a reducing agent. (4) Reaction products were purified in various chromatographic systems and were characterized by combustion, specific activity, and spectral analyses. $^{99}$Tc emits β radiation. TSPC is a tetrasulfonic acid derivative within a general class of compound known as phthalocyanines. Phthalocyanines are not naturally occurring substances, but they have been reported to mimic the activities of naturally occurring porphyrins. The tissue distribution pattern of the product was studied in rats bearing tumors. Most of the [$^{99}$Tc] TSPC accumulated in the liver, kidneys, ovaries, and uterus, whereas tumor uptake occurred mainly in the exterior cell layers. The in vivo stability of the complex was evidenced by the absence of $^{99}$Tc accumulation in the thyroid and the stomach.

Weber et al. describe magnetic properties of transition metal derivatives of 4',4",4'''-Tetrasulfophthalocyanine. (5) The tetrasulfophthalocyanine complexes of manganese, iron, cobalt, nickel, and copper were prepared in high purity and the magnetic moments of these substances were determined both in the solid state and in solution.

SUMMARY OF THE INVENTION

It is an object of the present invention to provide an improved technique for the identification of the sentinel lymph node that is more accurate than known techniques.

It is also an object of the present invention to provide an improved technique for the identification of the sentinel lymph node that simplifies the identification procedure over known techniques.

The present invention accomplishes the above objectives and more by providing in one embodiment a radioactive or radio-labeled blue porphyrin for identifying the sentinel lymph node or nodes. In the embodiment, a blue porphyrin is labeled with Technetium-99m, (Tc99m), which emits γ radiation. The radio-labeled blue porphyrin is injected into tissue surrounding a tumor lesion of a subject or into tissue surrounding the biopsy cavity in cases where the tumor has been previously excised. The injection of the radioactive chemical compound thereby stains the lymphatic channels to help identify that particular first node or sentinel node draining the area by using the blueish color as well as a Geiger counter. The technique of the present invention is for use in a sentinel lymph node biopsy in breast cancer or any other cancer or situation where the sentinel lymph node needs to be identified.

The advantage of the present invention is that it combines in one compound and one injection the procedure that previously required two different compounds and two separate injections. The present invention in one embodiment therefore comprises a single purified porphyrin, rather than a mixture of porphyrins as in the known art. And, the present invention uses sodium salt instead of the ammonium salt of the known art.

The present invention in another embodiment comprises a non-radioactive metal (manganese in a preferred embodiment) attached to the porphyrin compound for identification of the sentinel lymph node using a Magnetic Resonance Imaging (MRI) examination.

In summary, the present invention in one embodiment provides a detectably labeled porphyrin compound.

The present invention in another embodiment provides a method of producing the detectably labeled porphyrin compound, comprising the steps of: preparing a stannous chloride solution; adding Tc-99m-sodium pertechnetate solution into the stannous chloride solution to create a mixture; stirring the mixture at room temperature; adding purified phthalocyanine tetrasulfonate (PCTS) to the mixture; stirring the mixture again at room temperature; incubating the mixture at room temperature; and passing the mixture through a filter.

The present invention in another embodiment provides a method of identifying a sentinel lymph node, comprising the steps of: injecting the detectably labeled porphyrin compound into a tumor, wherein the porphyrin compound is detectably labeled with a radiolabel which is a γ-emitting radioactive metal; and detecting radioactive emission or a color so as to detect and thereby identify the sentinel lymph node.

The present invention in another embodiment provides a method of identifying a sentinel lymph node, comprising the steps of: injecting the detectably labeled porphyrin compound into tissue surrounding a tumor, wherein the porphyrin compound is detectably labeled with a non-radioactive metal; and taking a series of magnetic resonance images to identify the sentinel lymph node by viewing the images showing the injected detectably labeled porphyrin compound.

DETAILED DESCRIPTION OF THE INVENTION

As used in this application, a "porphyrin compound" means and includes any porphyrin, porphyrin analog or homolog, or derivative of a porphyrin or porphyrin analog or homolog. In a presently preferred embodiment the porphyrin compound is a blue porphyrin such as phthalocyanine tetrasulfonate. The porphyrin compound could also be phthalocyanine, hematoporphyrin, metalloporphyrin, or metallo phthalocyanine.

Furthermore, as used in this application, a "radioactive metal" includes radioactive metals such as Technetium 99, Iron 52, Indium 111, and Manganese 52.

As will be described in more detail below, the present invention in one embodiment provides a detectably labeled porphyrin compound. The porphyrin compound may be a blue porphyrin. The blue porphyrin may be phthalocyanine tetrasulfonate. The porphyrin compound may be detectably labeled with a radiolabel which is a γ-emitting radioactive metal. The γ-emitting radioactive metal may be Technetium-99m ($^{99m}Tc$).

Alternatively, the porphyrin compound may be detectably labeled with a non-radioactive metal. The non-radioactive metal may be manganese. The porphyrin compound may be a blue porphyrin. The blue porphyrin may be phthalocyanine tetrasulfonate.

The present invention in another embodiment provides a method of producing the detectably labeled porphyrin compound, comprising the steps of: preparing a stannous chloride solution; adding Tc-99m-sodium pertechnetate solution into the stannous chloride solution to create a mixture; stirring the mixture at room temperature; adding purified phthalocyanine tetrasulfonate (PCTS) to the mixture; stirring the mixture again at room temperature; incubating the mixture at room temperature; and passing the mixture through a filter. The stannous chloride solution may be at a concentration of 0.02 mmole/100 μl of 0.1 N Hcl. The Tc-99m-sodium pertechnetate solution may be at a ratio of 30.0 mCi/200 ul of normal saline. The phthalocyanine tetrasulfonate (PCTS) added to the mixture may be at pH 8.2. The first stirring step may last for two minutes. The second stirring step may last for five minutes. The incubating step may last for thirty minutes. The filter may be a 0.22 μm filter. The method may further comprise the step of purifying the porphyrin.

The present invention in another embodiment provides a method of identifying a sentinel lymph node, comprising the steps of: injecting the detectably labeled porphyrin compound into a tumor, wherein the porphyrin compound is detectably labeled with a radiolabel which is a γ-emitting radioactive metal; and detecting radioactive emission or a color so as to detect and thereby identify the sentinel lymph node.

In this method of identifying a sentinel lymph node according to this embodiment, the detectably labeled porphyrin compound may be injected into tissue surrounding the tumor of a subject so as to stain lymphatic channels and lymph nodes of the subject. The method may further comprise the step of massaging the tissue to facilitate flow of the detectably labeled porphyrin compound into the lymphatic channels and the lymph node. The method may further comprise the step of performing a lympho-scintigram to delineate the sentinel lymph node draining the detectably labeled porphyrin compound. The method may further comprise the step of detecting a highest amount of radioactivity at a site different from the tumor. The method may further comprise the step of making a skin incision over the site of the highest amount of radioactivity and following the lymphatic channels stained with the color to identify the sentinel lymph node. The method may further comprise the step of detecting the tumor using ultrasound. The method may further comprise the step of injecting the radio-labeled porphyrin compound into tissue surrounding a biopsy cavity so as to stain lymphatic channels and lymph nodes of the subject.

In this method of identifying a sentinel lymph node, the porphyrin compound may be a blue porphyrin. The blue porphyrin may be Tc-99m-phthalocyanine tetrasulfonate. The γ-emitting radioactive metal may be Technetium-99m (Tc99m).

The present invention in another embodiment provides a method of identifying a sentinel lymph node, comprising the steps of: injecting a detectably labeled porphyrin compound into tissue surrounding a tumor, wherein the porphyrin compound is detectably labeled with a non-radioactive metal; and taking a series of magnetic resonance images to identify the sentinel lymph node by viewing the images showing the injected detectably labeled porphyrin compound. The non-radioactive metal may be manganese. The porphyrin compound may be a blue porphyrin. The blue porphyrin may be phthalocyanine tetrasulfonate.

In more detail, the present invention in one embodiment provides a radioactive or radio-labeled blue porphyrin for identifying the sentinel lymph node or nodes. A blue porphyrin is labeled with Technetium-99m (Tc99m) and is injected into tissue surrounding a tumor lesion of a subject or into tissue surrounding the biopsy cavity in cases where the tumor has been previously excised. The injection of the radioactive chemical compound thereby stains the lymphatic channels to identify the particular first node or sentinel node draining the area by using the blueish color and a Geiger counter to detect the radioactivity emitted from the node. The technique of the present invention is for use in a sentinel lymph node biopsy.

The present invention in one embodiment therefore acts as a dye that stains the lymphatic channels of the body for identification of the sentinel lymph node. This dye was tested on rabbits and was successfully shown to stain the lymph nodes.

The effect of the present invention is that there is combined in one compound and one injection the procedure that previously required two different compounds and two separate injections. The single injection is therefore simpler than the known techniques and also increases the accuracy of the prior sentinel node identification methods.

EXPERIMENTAL DETAILS

The following example describes the preparation and administration results of Tc-99m Phthalocyanine Tetrasulfonate (Tc-99m-PCTS) according to one embodiment of the present invention. It is to be understood that the below description are examples provided for illustration purposes only, and other methods of preparation and administration may be used.

EXAMPLE 1

Preparation of Tc99m-PCTS

Into a freshly prepared stannous chloride solution (0.38 mg, 0.02 mmole/100 ul of 0.1 N Hcl) was added Tc-99m-sodium pertechnetate solution (30.0 mCi/200 ul of normal saline). The mixture was stirred magnetically at room temperature for two minutes. Into this mixture was added 2 ml of phthalocyanine tetrasulfonate (PCTS), pH 8.2, solution (100.2 mg, 0.12 mmole/2 ml) (TSW-V-135). The mixture was stirred at room temperature for five minutes, and then incubated at room temperature for thirty minutes. The product was passed through a 0.22 um filter. The radioactivity yield of the product prepared was 29.22 mCi (97.4%). The pH of the product was 7.8.

This next section describes the quality control of the above prepared solution. The radioactivity purity of the product was assayed by radiochromatography with whatman #1 paper and Instant Thin Layer Chromatography-silica gel (ITLC-SG) system and developed in acetone. One drop of sample was spotted on the chromatographic strip, air dried, and developed in 1 ml of acetone, respectively. The Rf value of the free pertechnetate (Tc-99m sodium pertechnetate) was 1.0 (solvent front). The Rf of the product was 0.0 (at origin). The chromatographic strips were cut into halves. The radioactivity of the top and bottom portion of the strips were measured in a dose calibrator, respectively. Thus, the amount of free pertechnetate was subtracted from the total activity. The radiochemical purity of the product was determined, as seen in the Table below.

TABLE

| Quality Control of Tc-99m PCTS | | |
|---|---|---|
| Media: | Acetone | Acetone |
| Strip: | Whatman #1 paper | ITLC-SG |
| | Rf = | Rf = |
| Tc-99m04: | 1.0 | 1.0 |
| TC-99m-PCTS: | 0.0 | 0.0 |
| Radioactivity: | uCi | uCi |
| Top portion strip | 0.1 (#1) | 0.1 (#1) |
| (Tc-99m04) | 0.1 (#2) | 0.1 (#2) |
| Bottom portion strip | 3.8 (#1) | 4.2 (#1) |
| | 3.4 (#2) | 4.4 (#2) |
| Total radioactivity | 3.9 (#1) | 4.3 (#1) |
| Total radioactivity | 3.5 (#2) | 4.5 (#2) |
| Radiochemical purity | 97.4% (#1) | 97.7% (#1) |
| of Tc-99m PCTS | 97.1% (#2) | 97.8% (#2) |
| Average | 97.3% | 97.8% |
| (TSW-V-137) | | |

Injection

The following three examples provide injection techniques for the injection of the radio-labeled blue porphyrin of the present invention into breast tumors. It is to be understood that the following examples are for illustration purposes only, and are not meant to limit the present invention in any way to those examples.

The blue porphyrin is labeled with Technetium-99m, as previously described, and is injected preoperatively. The injection technique depends on the presentation of the tumor. Three common scenarios are encountered (they are described as Examples 2–4 below).

EXAMPLE 2

Palpable Tumor Injection

The first scenario is a palpable tumor. In this scenario, the radio-labeled blue porphyrin acting as a dye is injected into the breast tissue surrounding the lesion. The injection sites are delineated by palpating the tumor and are usually located at 3, 6, 9 and 12 o'clock of the lesion. A 25-gauge needle may be used for the injection. The breast is massaged for at least five minutes to facilitate the flow of the dye into the lymphatics.

A pre-operative lympho-scintigram may be performed as early as five minutes following the injection to delineate the lymph node basin draining the radio-labeled substance. Alternatively, a gamma probe detector is used to locate and identify the sentinel lymph node. The gamma probe detector is attached to a signal processor that allows the surgeon to detect the amount of radioactivity by way of a digital readout or an audio sound. The highest point of radioactivity detected at a site different from the tumor is identified and, in the vast majority of cases, is located in the ipsi-lateral axilla. A skin incision is performed over the highest or hottest point and the blue lymphatic channels are identified and followed meticulously through the clavipectoral fascia to identify the sentinel lymph node. The gamma probe detector may also be used to help identify the location of the sentinel node. After excision of the blue and "hot" node, the axilla is evaluated for other blue and radioactive sites.

EXAMPLE 3

Malignant Lesion Injection

The second scenario is a malignant lesion detected by a mammogram or any other diagnostic modality such as ultra sound, magnetic resonance imaging, or others.

EXAMPLE 4

Biopsy Cavity Injection

The third scenario is a biopsy cavity following a lumpectomy for diagnosis.

In the second and third scenarios, the only difference is in the injection technique. For needle-localized lesions, the injection sites are guided with ultrasound detection of the tumors. In cases of microcalcifications, the injections are performed in the breast tissue surrounding the tumor in a plane parallel to the needle or guide wires placed in the malignant tumor under mammographic or sonographic guidance.

In cases where the tumor has been previously excised, the injection is in the tissue surrounding the biopsy cavity. One should attempt to avoid injection into the biopsy cavity. The injections could be assisted with sonographic detection of the biopsy cavity.

Therefore, the present invention improves the accuracy of known sentinel lymph node identification techniques and simplifies the identification procedure by providing in one embodiment a radio-labeled blue porphyrin for identifying the sentinel lymph node or nodes.

A further embodiment of the present invention is disclosed herein wherein a non-radioactive metal is attached to the blue porphyrin by way of a chemical reaction. In a preferred embodiment, the non-radioactive metal is Manganese (Mn). A Magnetic Resonance Imaging (MRI) exam will now show, using the technique of the present invention in this embodiment, the lymphatic channels and nodes, thus dispensing with the need for a lymphoscintigram. The Weber reference (5) describes a method of preparation of phthalocyanine having the Manganese attached reference.

The following describes a technique of Mn-Porphyrin and Magnetic Resonance Imaging using the Manganese-labeled molecule. It is to be understood that the description herein is for illustration purposes only, and other methods of preparation and administration may be used.

Technique

The scout images are taken first, then the patient is injected with the dye Mn-Porphyrin. The injection techniques are similar to the previously described methods. The area of injection is massaged, and the images are then taken serially using T1-weighted and T2-weighted sequences. The MRI examination is highlighted below.

MRI Examination

Body coil.

Scout image: FMPSPGR:TR/TE/FA:200/15/80 Acquire in 3 planes

T1 Axial/Sagittal, Coronal Spin Echo: TR/TE/FA:300/14/90 FOV:25 (adjust for size), Matrix: 256×192, slice thickness/gap:5/1,NEX:2, fat saturation.

T1 Axial/Sagittal, Coronal Gradient echo: TR/TE/FA:200/5.6/80, FOV:25, sat faturation (adjust for size), Matrix: 256×192, slice thickness/gap:5/1,NEX:1

T2 weighted ssFSE:TR/TE/FA:NA/96/90,FOV:25 (adjust for size), Matrix 256×192, slice thickness/gap:5/1,NEX: 0.5.

T2 weighted SE:TR/TE/FA:2000/100/90,FOV:25 (adjust for size), Matrix: 256×192, slice thickness/gap: 5/1, NEX:2.

REFERENCES

1. A. E. Giuliano, D. M. Kirgan, J. M. Guenther, D. L. Morton. Lymphatic Mapping and Sentinel Lymphadenectomy for Breast Cancer. Anals of Surgery, Vol. 220. No. 3. 391–401 (1994)
2. D. N. Krag, D. L. Weaver, J. C. Alex, J. T. Fairbank. Surgical Resection and Radiolocalization of the Sentinel Lymph node in Breast Cancer Using a Gamma Probe. Surgical Oncology, 2:335–340 (1993)
3. D. W. Wong. A Simple Chemical Method of Labeling Hematoporphyrin Derivative with Technetium-99m. J Label Compd & Radiopheam XX:351–361 (1983)
4. J. R. Rousseua, D. Autenrieth and J. E. Van Lier. Synthesis, Tissue Distribution and Tumor Uptake of Tc-99m Tetrasulfophthalocyanine. Int J Appl Radiat Isot, 34:571–579 (1983)
5. J. H. Weber, D. H. Busch, Complexes Derived from Strong Field Ligands. XIX. Magnetic Properties of Transition Metal Derivatives of 4,4',4",4'''-Tetrasulfophthalocyanine. Inorganic Chemistry, Vol. 4(4), 469–471 (1965).

What is claimed:

1. A method of identifying a sentinel lymph node, comprising the steps of:
   injecting a detectably labeled porphyrin compound into tissue surrounding a tumor, wherein the detectably labeled porphyrin compound includes a phthalocyanine tetrasulfonate and is detectably labeled with a non-radioactive metal; and
   taking a series of magnetic resonance images to identify the sentinel lymph node by viewing the images showing the injected detectably labeled porphyrin compound.

2. A method of identifying a sentinel lymph node, comprising the steps of:
   injecting a detectably labeled porphyrin compound into tissue surrounding a tumor, wherein the detectably labeled porphyrin compound includes a phthalocyanine tetrasulfonate and is detectably labeled with a non-radioactive metal; and
   taking a series of magnetic resonance images to identify the sentinel lymph node by viewing the images showing the injected detectably labeled porphyrin compound,
   wherein the non-radioactive metal is manganese.

3. The method of claim 1, further comprising taking one or more scout images prior to said injecting of the detectably labeled porphyrin compound.

4. The method of claim 1, further comprising massaging an area of injection prior to the taking of the series of the magnetic resonance images.

5. A method of identifying a sentinel lymph node, comprising the steps of:
   injecting a detectably labeled porphyrin compound into tissue surrounding a tumor, wherein the detectably labeled porphyrin compound includes a phthalocyanine tetrasulfonate and is detectably labeled with a non-radioactive metal; and
   taking a series of magnetic resonance images to identify the sentinel lymph node by viewing the images showing the injected detectably labeled porphyrin compound,
   wherein the magnetic resonance images are taken serially using T1-weighted and T2 weighted sequences.

6. The method of claim 2, further comprising taking one or more scout images prior to said injecting of the detectably labeled porphyrin compound.

7. The method of claim 2, further comprising massaging an area of injection prior to the taking of the series of the magnetic resonance images.

8. The method of claim 2, wherein the magnetic resonance images are taken serially using T1-weighted and T2 weighted sequences.

* * * * *